US010682483B2

(12) United States Patent
Thorgaard

(10) Patent No.: US 10,682,483 B2
(45) Date of Patent: Jun. 16, 2020

(54) APPARATUS AND METHOD FOR DELIVERING A GAS MIXTURE TO A CHILD

(71) Applicant: Iltsut ApS, Vedbaek (DK)

(72) Inventor: Per Thorgaard, Aalborg (DK)

(73) Assignee: Iltsut ApS, Vedbaek (DK)

(*) Notice: Subject to any disclaimer, the term of this patent is extended or adjusted under 35 U.S.C. 154(b) by 776 days.

(21) Appl. No.: 15/306,593

(22) PCT Filed: Apr. 24, 2015

(86) PCT No.: PCT/EP2015/058905
§ 371 (c)(1),
(2) Date: Oct. 25, 2016

(87) PCT Pub. No.: WO2015/162255
PCT Pub. Date: Oct. 29, 2015

(65) Prior Publication Data
US 2017/0043112 A1    Feb. 16, 2017

(30) Foreign Application Priority Data
Apr. 25, 2014 (EP) .................................... 14165976

(51) Int. Cl.
*A61M 16/06* (2006.01)
*A61M 16/08* (2006.01)
(Continued)

(52) U.S. Cl.
CPC ........ *A61M 16/0683* (2013.01); *A61J 7/0053* (2013.01); *A61J 17/001* (2015.05);
(Continued)

(58) Field of Classification Search
CPC .............. A61M 16/0683; A61M 16/14; A61M 16/101; A61M 16/125; A61M 16/0672;
(Continued)

(56) References Cited

U.S. PATENT DOCUMENTS 2,268,145 A    12/1941   Culter et al.
5,462,050 A * 10/1995   Dahlstrand ........... A61M 16/06
                                                                           128/205.25
(Continued)

FOREIGN PATENT DOCUMENTS

GB         2277688 A    11/1994
WO      02094361 A1    11/2002
(Continued)

*Primary Examiner* — Timothy A Stanis
*Assistant Examiner* — Margaret M Luarca
(74) *Attorney, Agent, or Firm* — Dinsmore & Shohl LLP

(57) ABSTRACT

The invention concerns an apparatus for delivering a gas mixture to the nasal airways of a spontaneously breathing child, the apparatus comprises a soother (11), a body (1) forming a mixing chamber attached to the soother and adapted for positioning over the nostrils of the child, at least one gas delivering hose (2) attached to the body forming the mixing chamber for supplying gas to the mixing chamber, wherein the mixing chamber has access to the surrounding air and is adapted for mixing the supplied gas with the surrounding air in order to provide a gas mixture for nasal inhalation, and wherein the body forming the mixing chamber comprises an edge portion (8) with at least one non-contact section, which is adapted for having no contact with the child when the apparatus is in use thereby providing access from the surrounding air to the mixing chamber.

26 Claims, 8 Drawing Sheets

(51) Int. Cl.
*A61J 17/00* (2006.01)
*A61M 15/00* (2006.01)
*A61M 16/12* (2006.01)
*A61J 7/00* (2006.01)
*A61M 16/10* (2006.01)
*A61M 16/14* (2006.01)

(52) U.S. Cl.
CPC ........ *A61J 17/006* (2015.05); *A61M 15/0086* (2013.01); *A61M 16/06* (2013.01); *A61M 16/0672* (2014.02); *A61M 16/0816* (2013.01); *A61M 16/101* (2014.02); *A61M 16/125* (2014.02); *A61M 16/14* (2013.01); *A61M 2016/1025* (2013.01); *A61M 2202/0208* (2013.01); *A61M 2205/3334* (2013.01); *A61M 2205/70* (2013.01); *A61M 2205/75* (2013.01); *A61M 2210/0618* (2013.01); *A61M 2240/00* (2013.01)

(58) Field of Classification Search
CPC .............. A61M 16/0816; A61M 16/06; A61M 16/086; A61M 16/0666; A61M 16/0488; A61M 16/049; A61M 17/006; A61M 15/0021
See application file for complete search history.

(56) References Cited

U.S. PATENT DOCUMENTS

| | | | |
|---|---|---|---|
| 6,526,966 | B1 | 3/2003 | Peesay |
| 6,626,168 | B1 | 9/2003 | Carroll et al. |
| 8,707,950 | B1 * | 4/2014 | Rubin ................... A61M 16/06 128/202.27 |
| 9,675,774 | B2 * | 6/2017 | Cipollone ......... A61M 16/0666 |
| 2009/0050156 | A1 * | 2/2009 | Ng ........................ A61M 16/06 128/205.24 |
| 2010/0000525 | A1 | 1/2010 | Lee et al. |
| 2010/0147298 | A1 | 6/2010 | Loescher et al. |
| 2012/0318265 | A1 | 12/2012 | Amirav et al. |
| 2013/0118485 | A1 * | 5/2013 | Shahaf ................ A61M 15/00 128/202.15 |

FOREIGN PATENT DOCUMENTS

| | | |
|---|---|---|
| WO | WO-2006125610 A1 | 11/2006 |
| WO | WO-2007047286 A2 | 4/2007 |
| WO | 2011125061 A2 | 10/2011 |
| WO | WO-2011137905 A1 | 11/2011 |
| WO | WO-2012018362 A1 | 2/2012 |

* cited by examiner

Test Parameters

| Test Item | O2 Flow lt Set | Mechanical Lung Settings | | | |
|---|---|---|---|---|---|
| | | Tidal Volume | Respiration Rate | Minut Volume | Inspiratory Flow |
| 2L.6INSP | 2l/min | 40ml | 40bpm | 1,6l | 6l/min |
| 2L.9INSP | 2l/min | 80ml | 30bpm | 2,4l | 9l/min |
| 2L.12INSP | 2l/min | 120ml | 25bpm | 3,0l | 12l/min |
| 3L.6INSP | 3l/min | 40ml | 40bpm | 1,6l | 6l/min |
| 3L.9INSP | 3l/min | 80ml | 30bpm | 2,4l | 9l/min |
| 3L.12INSP | 3l/min | 120ml | 25bpm | 3,0l | 12l/min |
| 4L.6INSP | 4l/min | 40ml | 40bpm | 1,6l | 6l/min |
| 4L.9INSP | 4l/min | 80ml | 30bpm | 2,4l | 9l/min |
| 4L.12INSP | 4l/min | 120ml | 25bpm | 3,0l | 12l/min |

Fig 8

APPARATUS AND METHOD FOR DELIVERING A GAS MIXTURE TO A CHILD

FIELD OF INVENTION

The invention relates to an apparatus for providing a mixture of at least two gases to the nasal airway of a spontaneously breathing child.

BACKGROUND OF THE INVENTION

Supplying a gas mixture with a specified concentration—such as oxygen enriched air—to a child in a simple manner can be difficult. Firstly, the gas mixture should be of a known and preferably of a constant mixture in the child's airways, for example a known and constant oxygen percentage—or percentage interval. Secondly, the gas should be provided by an apparatus ensuring avoidance of unintentional "continuous positive airway pressure" (CPAP). Thirdly, the gas mixture should be delivered in a way ensuring a stable positioning of the gas delivery apparatus thereby avoiding intensive staff surveillance and repositioning of the apparatus.

As an example of known solutions, WO 2011/137905 A1 discloses a soother, having a mouth shield, provided with fluid guides adapted for guiding a fluid to the nostrils of a child. The fluid guides are engageable with a back side of the mouth shield and the fluid guides are connected with a fluid delivering source. The fluid source provides oxygen which via the fluid guides is directed towards the nostrils of the child. The child will then inhale the provided oxygen and the surrounding air.

GB 2 277 688 A discloses a device for delivering of gas with anaesthetic vapours to children. The device comprises a teat, a mask tightly sealed to the face around the nose to prevent the escape of gases. By providing a mask which is closed, the gas provided to the device needs to be pre-mixed. If one desires to deliver oxygen enriched air the addition of oxygen needs to take place before the gas enters the mask. This results in a relatively complex system. In addition, when using a closed mask there is a need for constant surveillance of the child in case of a malfunction of the gas supply or in case nasal mucus blocks the gas inlet of the mask.

Another known solution is known from US 2010/0000525 A1, wherein an auxiliary device for an aerosol therapy unit with a main body and a delivery tube. The main body includes a bendable retention plate extending downwardly from a nipple connecting portion to which the delivery tube is retained. However, this solution does not ensure a known and preferably of a constant mixture gas and air in the child's airways. Furthermore, the device is bulky and would need for constant surveillance of the child in case the child moves as the retention of the delivery tube will constrain the movements that the child may do without interfering with the delivery tube.

SUMMARY OF THE INVENTION

Considering the above, it is an object of the present invention to provide an apparatus for supplying a gas mixture with a specified concentration or concentration range—such as oxygen enriched air—to a child in a simple manner.

In an aspect the objects of the present invention can be achieved by an Apparatus for delivering a gas mixture to the nasal airways of a spontaneously breathing child, the apparatus comprises a soother, a body forming a mixing chamber attached to the soother and adapted for positioning over the nostrils of the child, at least one gas delivering hose attached to the body forming the mixing chamber for supplying gas to the mixing chamber, wherein the mixing chamber has access to the surrounding air and is adapted for mixing the supplied gas with the surrounding air in order to provide a gas mixture for nasal inhalation and wherein the body forming the mixing chamber comprises an edge portion with at least one non-contact section, which is adapted for having no contact with the child when the apparatus is in use thereby providing access from the surrounding air to the mixing chamber.

Thus, it is possible to deliver a desired gas mixture to the airways of a child. For example, by mixing a gas with a known oxygen concentration (gas supplied by hoses) with ambient air (gas supplied by holes penetrating the body forming the mixing chamber and leaks along the edge portion of the mixing chamber) a known average oxygen concentration or average concentration interval in the airways of the child can be achieved. The achieved oxygen concentration in the airways of the child relates to the oxygen concentration in the supplied gas from the hose and the breathing pattern of the child as documented in experimental studies as described below.

Further, the soother ensures that the body forming the mixing chamber is positioned correctly on the face of the child. A soother will also comfort the child. Children have sucking reflexes so the soother will be kept in place; the sucking reflexes are even present during sleep. When a child has a soother in the mouth it will nose breath; thus ensuring that the child breaths the oxygen enriched air via the mixing chamber.

The body forming a mixing chamber is preferably formed such that the nose of the child is covered and such that the mouth is not covered.

The child can be a preterm baby and/or a child still having sucking reflexes in order to ensure that the mixing chamber are kept over the nostrils of the child.

The gas mixture delivered to the nasal airways can, for example, be oxygen enriched air with 40 to 55% oxygen. The mixing chamber is used for mixing the gas supplied by the hoses, such as oxygen, with the surrounding air which accesses the mixing chamber via the accesses provided for by the apparatus. As the mixing chamber has access to the surroundings there is no overpressure in the mixing chamber, which ensures the absence of Continous Positive Airway Pressure (at recommended flow rates). This is contrary to the function of the CPAP mask where application of overpressure is intended. When using the present invention according to the first aspect the respiration of the child takes place entirely unassisted.

Preferably, the flow rate of the supplied gas is less than 4 litres pr. minute, whereby it is ensured that the child is not irritated by the flowing gas from the hoses and minimising the risk of drying out the nasal mucosa.

The flow of the supplied gas can be adapted to the age and respiratory performance of the child and preferably according to recommendations based on an experimental model as well as the achieved effect on oxygenation in the specific clinical case.

The supplied gas can be delivered via the hoses from a pressurised gas source equipped with a flow regulator/indicator.

The body forming the mixing chamber can be a concave shaped body. In an embodiment the body forming the mixing chamber comprises a plastic material and/or a mesh, preferably a wire mesh. The plastic material can be polyurethane, such as polyurethane foam which is comfortable when in contact with the skin, as an alternative or in combination herewith the plastic material can be silicone, soft vinyl and/or thermoplastic elastomer.

In an embodiment, the body forming the mixing chamber is attached to the soother by use of a flexible band. The flexible band can be an elastic band. The flexible band can engage a handle of a soother in order for a detachable attachment of the body forming the mixing chamber to the soother.

Preferably, gas via the hoses is supplied continuously. This makes the supplying of the gas relatively simple as only a constant flow rate is to be ensured.

In an embodiment, the body forming the mixing chamber comprises at least one penetrating hole for providing access to the surrounding air. In other words, the body forming the mixing chamber can be penetrated by at least one hole. The at least one penetrating hole can be placed such that the free access to ambient air is preserved in case of increased secretion from the nose of the child. For example the at least one penetrating hole can be positioned in the region of the body forming the mixing chamber closest to the tip of the nose.

Advantageously, the body forming the mixing chamber comprises an edge portion, and wherein the at least one penetrating hole is provided in the body forming the mixing chamber at least 5 mm from the edge portion, preferably 10 mm. Thus, it can be ensured that the at least one penetrating hole is positioned such that it will not clog in case nasal mucus or other secretion gets inside the mixing chamber.

In an embodiment, the mixing chamber has access to the surrounding air at least partly by at least one non-contact section of the edge portion which is adapted for having no contact with the child when the apparatus is in use. The body forming the mixing chamber can thus be positioned over the nostrils of the child and stay free and only touch the face of the child in a few sections hereby ensuring an air passage between the face of the child and the body forming the mixing chamber. The body forming the mixing chamber can then be made such that the edge portion is not pressed against the face of the child which makes it more comfortable to use and the child will not feel that something covers his or hers nose. Further, having non-contact sections of the edge portion ensures that nasal mucus and/or vomit and/or another body fluid can exit the body forming the mixing chamber so as to not hinder free respiration of the child. Preferably, at least 10% of the edge portion is not in contact with the face of the child.

In an embodiment, the body forming the mixing chamber comprises an edge portion wherein a section of the edge portion is adapted for being in contact with the nasal dorsum of the child. The edge portion may advantageously be provided with indentations on each side to ensure non-contact sections through which ambient air may be drawn into the mixing chamber.

Advantageously, the gas supplied via the at least one gas delivering hose is oxygen. Thus, the apparatus can be used for oxygen therapy. The features of the present invention make it especially suitable for use in administering oxygen to a patient where little surveillance of the patient is needed.

In an embodiment, the apparatus further comprises a system for administering aerosolized medication to the mixing chamber, preferably, by use of a nebulizer. Thus is it possible to treat, for example, respiratory diseases.

In an embodiment, the apparatus comprises two gas delivering hoses. The two hoses may be connected and/or formed of one hose which has openings for supplying gas to the mixing chamber.

Preferably, the body forming the mixing chamber comprises an edge portion having a substantially triangular or heart shaped form. Further, the body forming the mixing chamber may be provided with a dome-like shape. If the edge portion has a substantially triangular shape one corner of the body forming the mixing chamber can be positioned over the nasal dorsum of the child and the opposite side can be attached to a soother for example by use of an flexible band, as mentioned above. In similar fashion an edge portion with a substantially heart shaped form can be positioned such that the tip of the heart shape can be positioned just over the nasal dorsum of the child, the heart shape will so to speak be positioned upside down around the area of the nostrils.

In an embodiment, the at least one gas delivering hose is adapted to engage with the soother for attaching the body forming the mixing chamber to the soother. This results in a simple construction. Preferably, the hose is flexible but rigid so that the apparatus is firmly fixated to the soother. In an example, the at least one gas delivering hose engage with the handle of the soother by fitting it tightly around at least a part of the handle. Preferably, a flexible band is used for tightening the at least one hose to the handle.

In an embodiment, the hose is adapted to be guided over the jaw region and away from the face of the child. Hereby it is ensured that the hose is of minimal nuisance to the child. Further, guiding the hose away from the face of the child will ensure that it appear as discretely as possible. This will bring comfort to the parents and family when looking at the child.

In a preferred embodiment, the body forming the mixing chamber is made of a soft, resilient material, such as silicone or the like. Furthermore, it is found advantageous that the body forming the mixing chamber is softer along the edge portion than in the central portion. This softness of the edge portion may be achieved by the provision of a thinner material in the edge portion than in the central portion. Hereby, it is ensured that the mixing chamber is comfortable for the child.

In addition or as an alternative to the above, the body forming the mixing chamber comprise a mesh.

In an embodiment the soother comprises a strap suitable for keeping the soother in the mouth and thus the body forming the mixing chamber in place. The strap can be positioned around the head of the child for ensuring that the soother is kept in the mouth. Preferably, the strap has an adjustable length.

In a further aspect the invention regards a method for delivering a gas mixture to a child comprising the steps of, providing a mixing chamber for positioning over the nostrils of the child such that the child inhales the gas mixture flowing through the mixing chamber, supplying a gas to the mixing chamber, and providing access for the surrounding air to the mixing chamber, wherein the mixing chamber is used for mixing the supplied gas and the surrounding air into a mixed gas to be inhaled by the child. Thus, it is possible to ensure that a desired gas mixture can be delivered and inhaled by a child. The gas mixture can for example be oxygen enriched air with a resultant oxygen content in the airways of the child between 35 and 65% oxygen, preferably between 40 to 53%. The access for the surrounding air to the mixing chamber ensures that there is no overpressure in the mixing chamber and that no forced overpressure is forced to the airways of the child. Overpressure can result in gas being forced into the oesophagus and into the stomach which is uncomfortable and can lead to vomiting.

Advantageously, the mixing chamber comprises an edge portion such that when the mixing chamber is positioned such that the access for the surrounding air, at least partly, is provided between the edge portion and the child. This makes the method both more secure and comfortable for the child.

Preferably, the access to the surroundings is at least partly provided by at least one hole penetrating the mixing chamber.

It is to be understood that the method can be adapted in similar ways as the apparatus.

DESCRIPTION OF THE DRAWINGS

The invention will in the following be described in greater detail with reference to the accompanying drawings:

FIG. 8 is a table with the test profiles corresponding to the measured data (graphs) shown in FIG. 7.

DETAILED DESCRIPTION OF THE INVENTION

Figure 1:
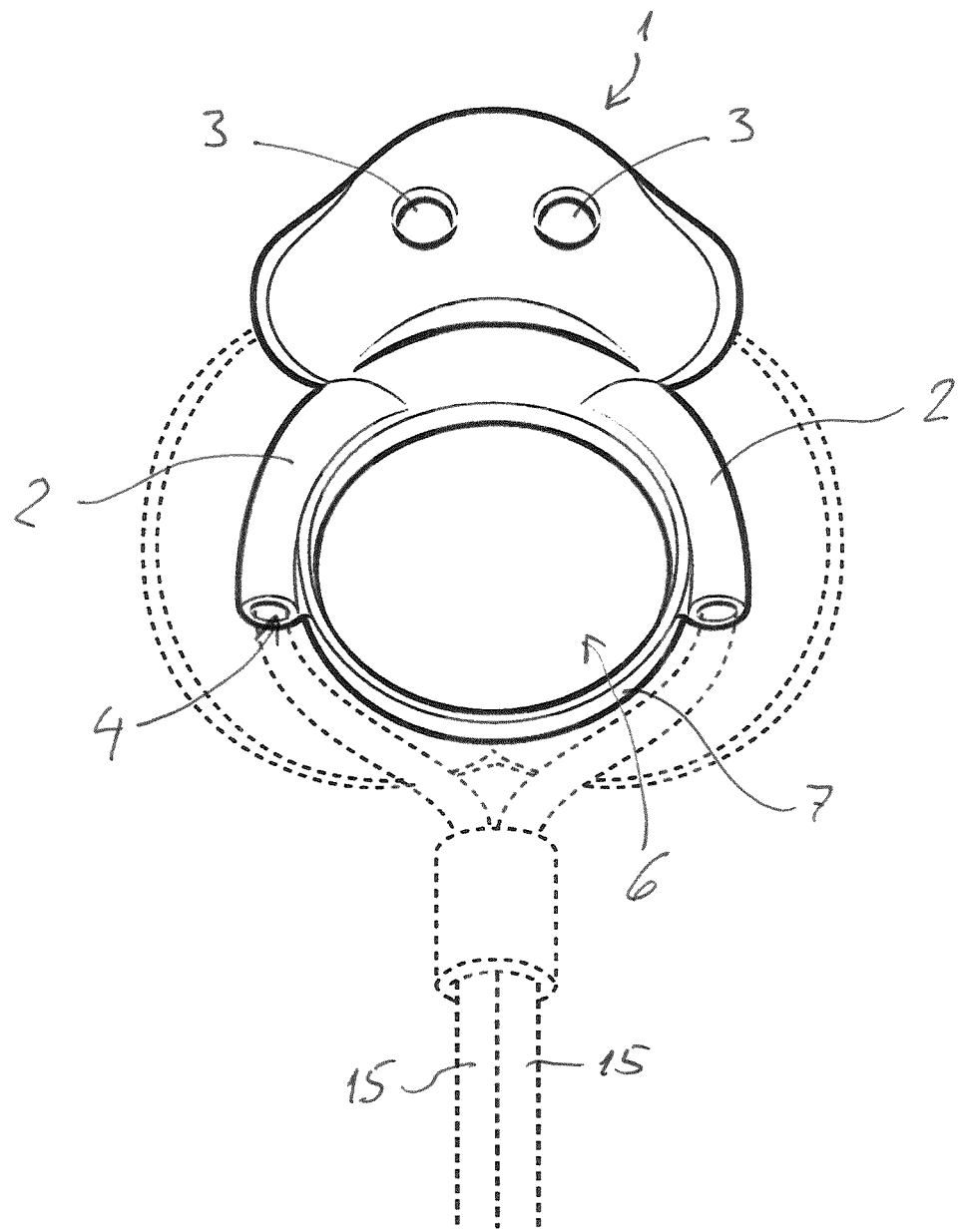
FIG. 1 is a schematic view of a body forming a mixing chamber according to an embodiment of the invention in a first view.

FIGS. 1-3 and 6 show a body forming a mixing chamber according to an embodiment of the invention from different angles. It discloses a body forming a mixing chamber 1 (will in the following be denoted mixing chamber) which is to be attached to a soother as can be seen in FIGS. 4 and 5. The mixing chamber 1 has two gas delivering hoses 2 for delivering gas to the mixing chamber 1 and a flexible, elastic band 7, which is used for attaching the mixing chamber 1 to a soother 11 (see the dotted lines in the FIGS. 1-3, 6 and FIGS. 4 and 5). The mixing chamber 1 has two penetrating holes 3 which penetrate the body forming the mixing chamber for providing an access for the surrounding air to the mixing chamber 1.

The mixing chamber 1 has a dome-like shape with the form of an oversized nose so that it can be positioned over the nostrils of a child hereby partly covering the nose but not the mouth.

The hoses 2 have gas inlets 4 which can be connected to supply hoses (shown in dotted lines) which supply the desired gas, preferably oxygen. The hoses 2 have gas outlets 5 inside the mixing chamber 1 such that the gas introduced in through the inlets 4 are supplied via the gas outlets 5 to the mixing chamber 1. The supply hoses 15 (in the dotted lines) are permanently mounted in the hoses 2 at the gas inlet 4.

The mixing chamber 1 shown in the figures can be made by injection moulding a plastic material. Preferably, the material used is silicone, soft vinyl and/or thermoplastic elastomer. The mixing chamber 1 can also be made, preferably partly, of a mesh. The mesh can be made of metal, carbon fibre and/or woven fabric such as gaze. Part of the mesh can be covered by a plastic material. The natural holes in the mesh can provide the mixing chamber 1 with access to the surrounding air.

It is preferred that the mixing chamber is soft but also dimensionally stable such that the size of the mixing chamber does not change when breathing. The mixing chamber is preferably made as an integral structure, in other words as one piece, as can be seen in the FIGS. 1 to 6.

The mixing chamber 1 has an edge portion 8 which defines the edges of the mixing chamber. The edge portion 8 has two indentations 9 on each side of the mixing chamber 1. These indentations 9 are adapted to fit with the mouth shield of a soother such that the upper edge of the mouth shield fits into the indentations 9 as can be seen on FIGS. 4 and 5.

The edge portion 8 has a section 10 which is adapted to get in contact with the nose of the child. Preferably, it gets in contact with the nasal dorsum of the child such that the tip of the nose is inside the mixing chamber 1. Advantageously, the edge portion 8 between the section 10 and the indentations 9 on each side of the mixing chamber does not get in contact with the skin of the child so that there is free flow passage for the surrounding air to the mixing chamber there between.

The mixing chamber 1 is preferably made soft by the material used. To ensure that the mixing chamber retains its dome-like shape and softness, the edge portion 8 is made softer than the central portion of the mixing chamber 1. This softness may be provided by providing a thinner material in the edge portion 8 than in the central portion of the mixing chamber 1.

Figure 2:
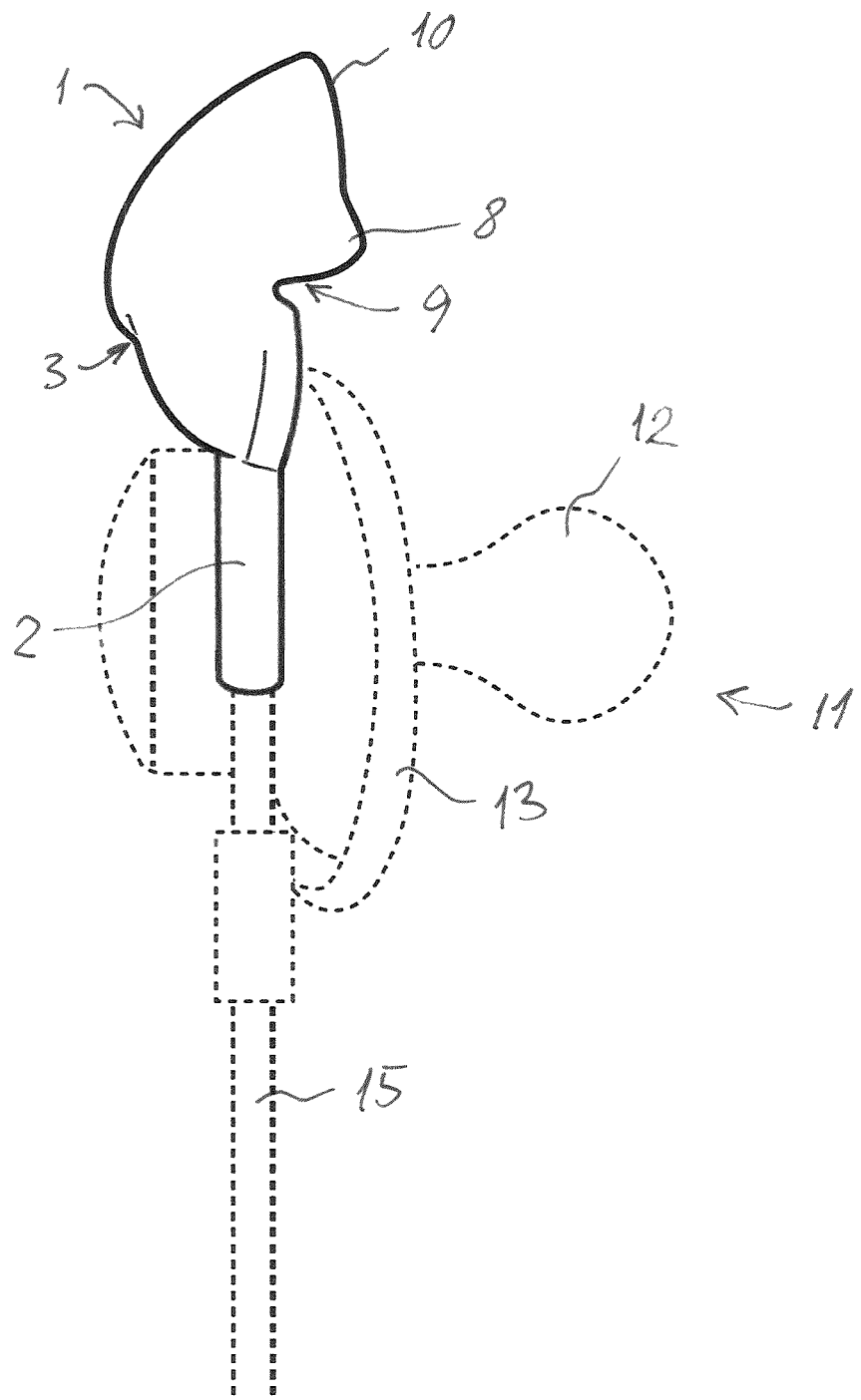
FIG. 2 is a schematic view of a body forming a mixing chamber according to an embodiment of the invention in a second view.
Figure 3:
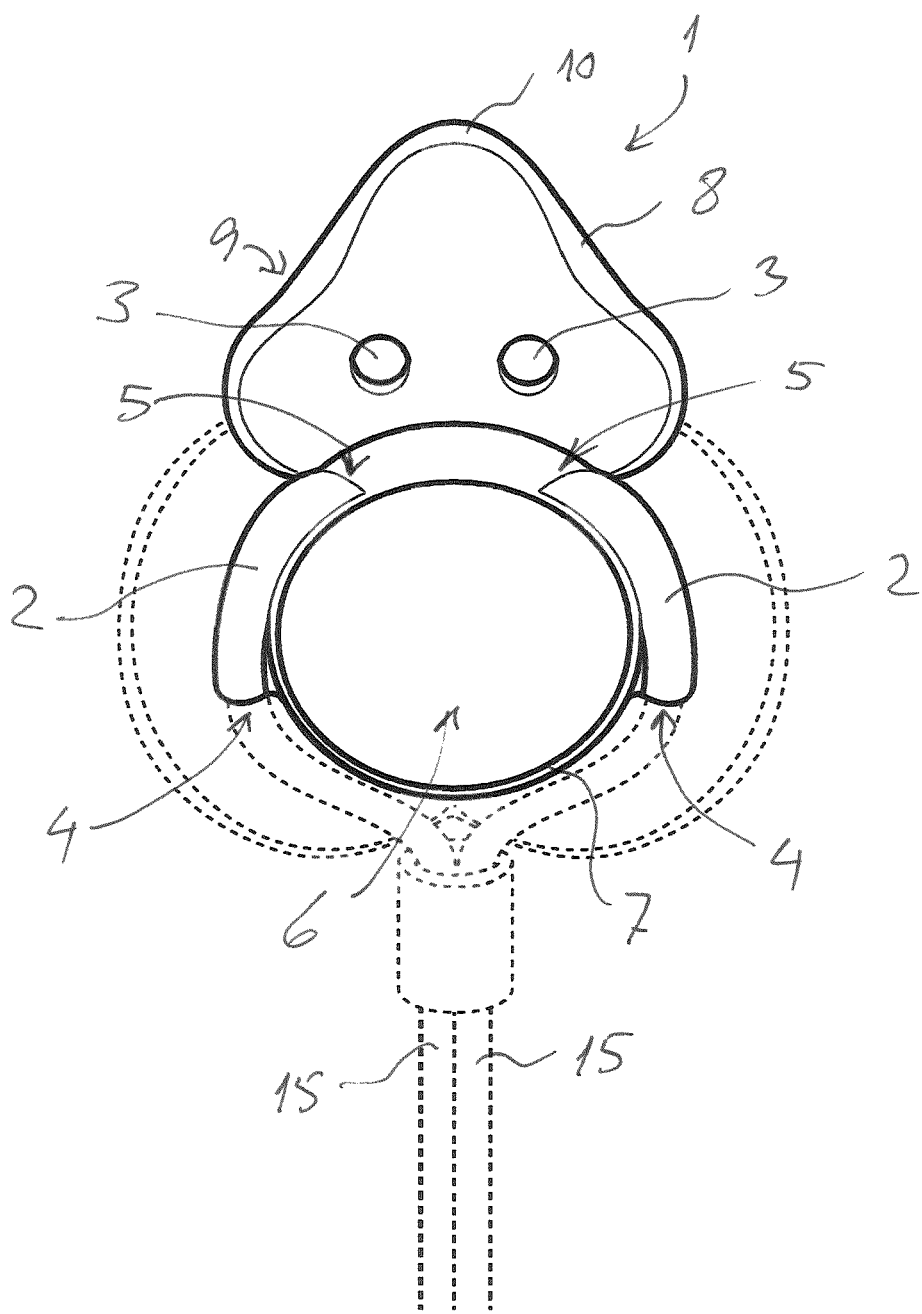
FIG. 3 is a schematic view of a body forming a mixing chamber according to an embodiment of the invention in a third view.
Figure 4:
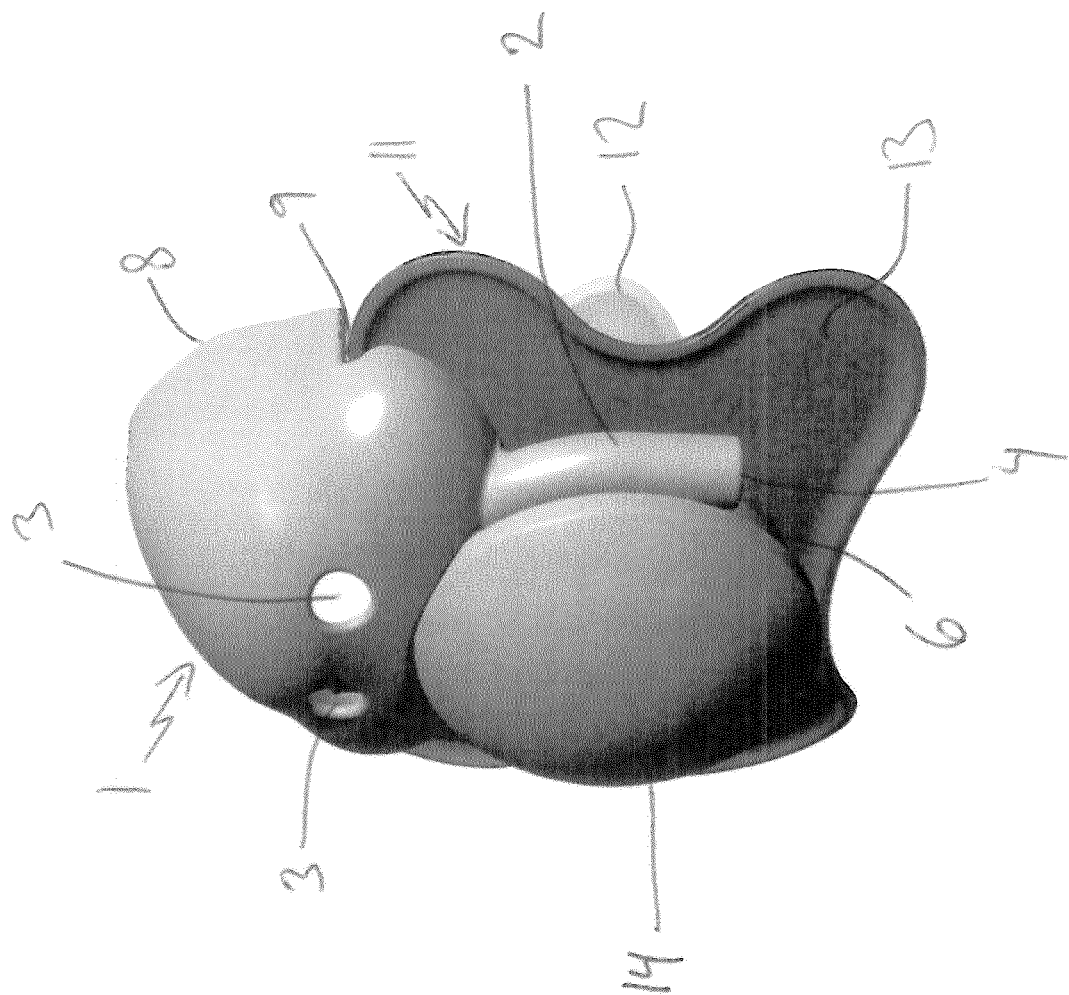
FIG. 4 is a schematic view of an embodiment of the invention in a first view.
Figure 5:
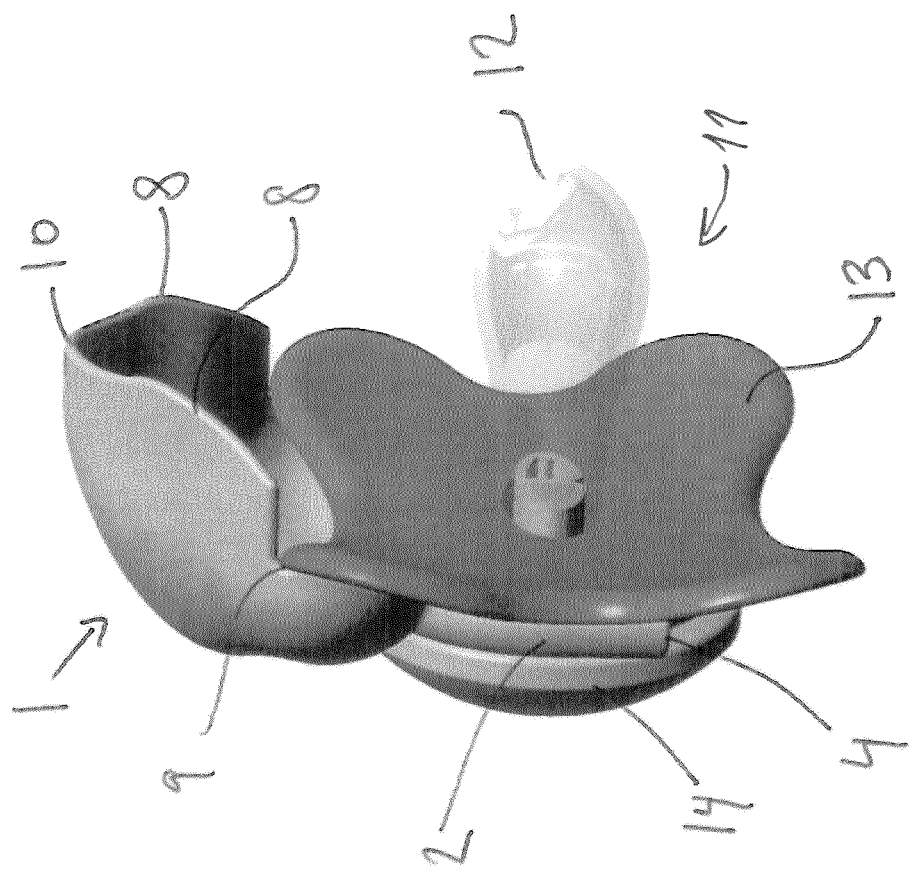
FIG. 5 is a schematic view of an embodiment of the invention in a second view.
Figure 6:
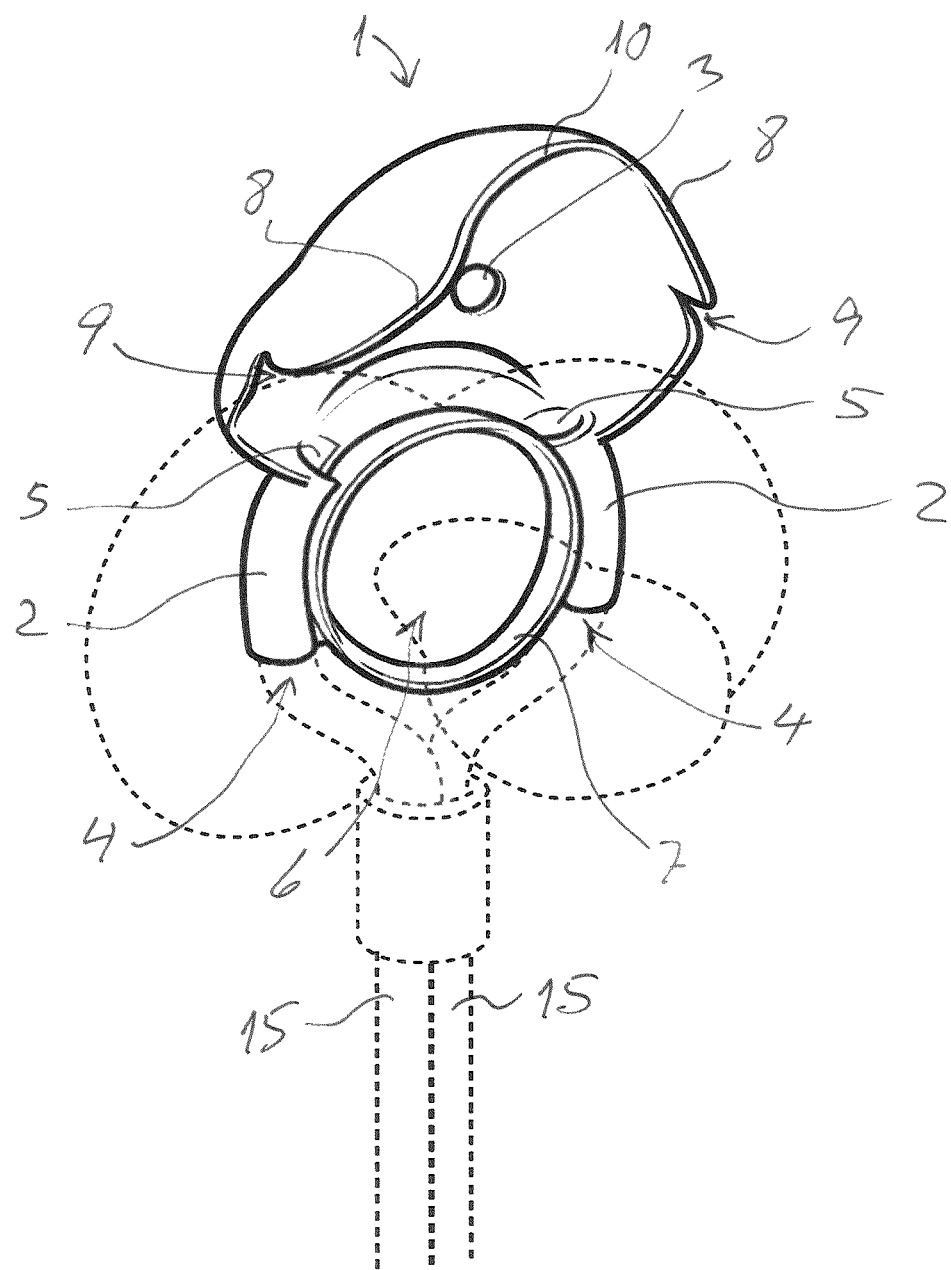
FIG. 6 is a schematic perspective view of the embodiment in FIGS. 1-3.

FIGS. 4 and 5 discloses an embodiment of the invention where the mixing chamber 1 as disclosed in the FIGS. 1, 2 and 3 is attached to a soother 11. The soother 11 has a teat 12 and a mouth shield 13. The edge of the mouth shield 13 is fitted into the indentations 9. This aids the positioning of the mixing chamber 1 such that it is kept in the correct position over the nose of the child. The mouth shield 13 has a handle 14 which is used to secure the mixing chamber 1 to the soother 11.

It is to be understood that the body forming the mixing chamber 1 and the soother can be an integral unit, such that the body forming the mixing chamber 1 cannot be separated from the soother 11 (shown in dotted lines).

Alternatively, the body forming the mixing chamber 1 can be releasably attached to the soother, as shown in the figures. Here the handle 14 of the soother is fitted into the opening 6 and is kept firmly in place by use of the flexible band 7. When using a flexible band 7 the mixing chamber 1 can be attached to a plurality of soother types and sizes. Thus, the child can use its own soother with the mixing chamber attached hereto, hereby giving the child the comfort of using his or hers own soother. The means for attaching, the flexible band 7, can be adapted to be used with all kinds of soothers on the market. The flexible band 7 can be made of a material that is highly elastic, such as a rubber band.

The hoses 2 partly form the opening 6 and contribute to ensuring that the mixing chamber 1 is kept in place. Preferably, the hoses 2 are flexible but more rigid than the flexible band 7 whereby the hoses 2 can be used to ensure the correct relative position of the mixing chamber 1 in relation to the soother.

In use the child puts the teat 12 in the mouth; this will normally initiate the sucking reflexes of the child and will keep the mixing chamber in place over the nostrils of the child. The section of the edge portion 10 which is farthest away from the mouth will touch the nasal dorsum of the child. The inlet 4 of the hoses 2 is connected to an oxygen delivering device which delivers a constant flow of oxygen. Arranged in that way, the mixing chamber will be positioned in such a way that access to the surrounding air is achieved at least via the penetrating holes 3 and the access provided between the edge portion 8 and the face of the child on each side of the nose (close to the cheeks). When the child inhales air via the mixing chamber, air is sucked from the surroundings into the mixing chamber hereby a mixing of the gases takes place.

When using an embodiment of the invention it can be advantageous to regulate the gas flow in order to ensure the supply of a constant gas mix to the child.

When using an embodiment of the invention the averaged oxygen concentration inhaled by the patient relates to the gasflow delivered by the hoses, the tidal volume, the respiratory rate and the inspiratory flow-rate.

Normally the tidal volume is in the range 8-10 ml/kg with a respiratory rate in the range between 20 to 40 bpm. (breaths per minute) The values for the tidal volume and the respiratory pattern varies over time depending on the mood of the child and other factors as e.g. medication. The flow rate of the gas provided by the hoses is preferably constant and up to 4 l/min (liters pr. minute).

Figure 7:
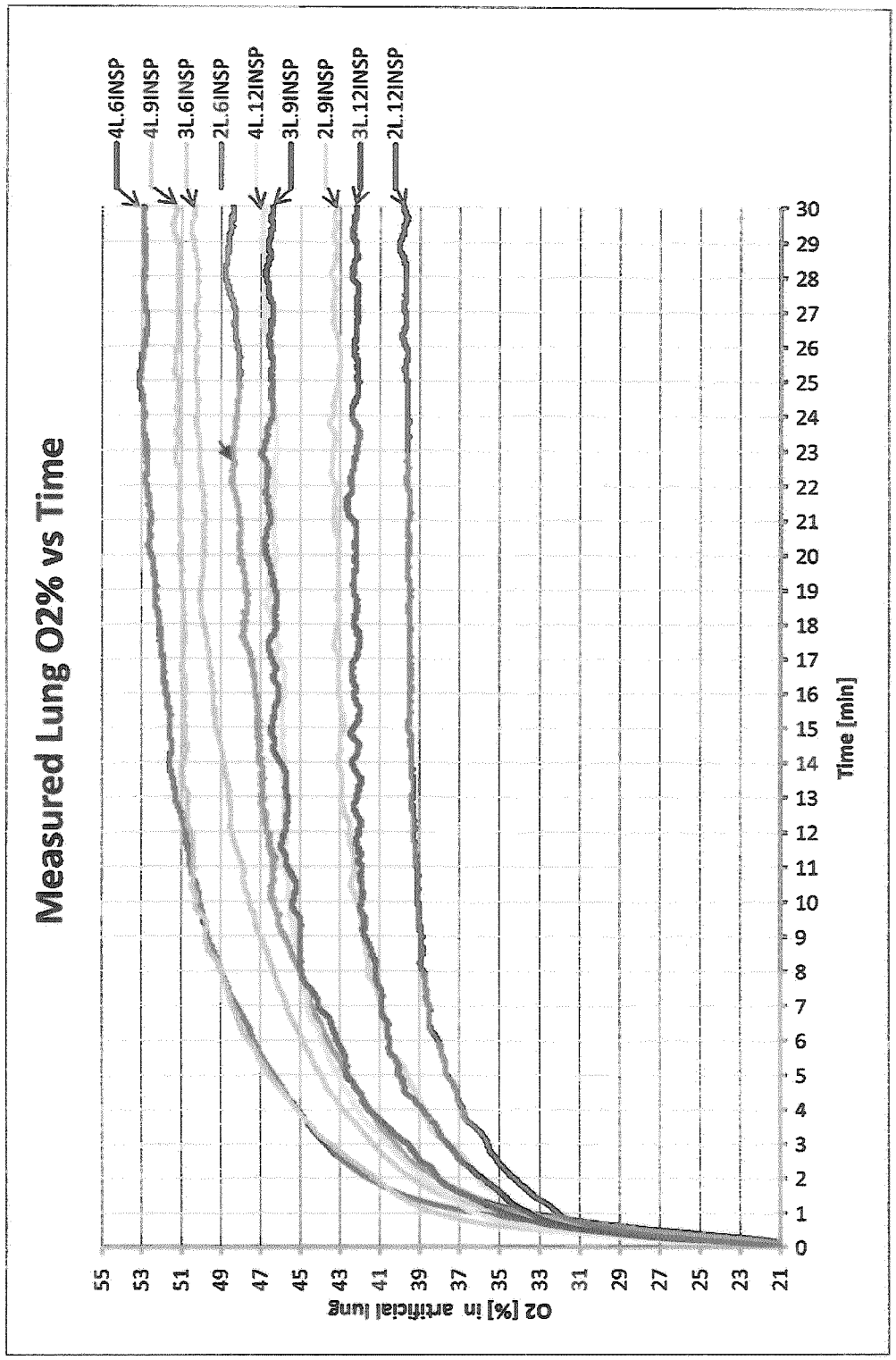
FIG. 7 is a series of graphs showing the measured data corresponding to the test profiles shown in FIG. 8.

FIG. 7 shows a selection of tests of an embodiment of the invention being attached to a dummy of a child which had an artificial respiratory system (airways and lungs). The tests were performed with pure oxygen being delivered via the hoses and at various flow rates of the oxygen provided by the hoses (2-4 liters per minute) and at various respiratory patterns (tidal volume, respiratory rate and inspiratory flow rate). The specific test profiles are shown in FIG. 8. The averaged oxygen concentration of inhaled air (expressed by the oxygen concentration in an artificial lung) was then measured as a function of time. The duration of time before a stable oxygen concentration is reached in the airways is caused by the residual capacity (volume) of air in the airways, lungs and in the ventilator system of the dummy and the hoses connecting the dummy to the ventilator and monitoring device for measurement of gas flow, oxygen concentration, etc.

In FIG. 7, the graph shows nine curves of the oxygen percentage measured in the artificial lung of the dummy as a function of time. The curves correspond to various test profiles as shown in FIG. 8. Thus tidal volumes of 40, 80 and 120 ml have been tested at various respiratory rates (40, 30 and 25 beats per minute) and at various inspiratory flow rates (6, 9 and 12 liters per minute). Each graph is "named" according to the test condition, as outlined in the left column of FIG. 8. The gas provided by the hoses is 100% oxygen with flow rates of 2, 3 or 4 liter per minute.

It can be seen that for all curves the oxygen concentration increases fast during the first few minutes reaching a stable value after 10-20 minutes. The duration of time before a stable oxygen concentration is reached is caused by the residual capacity (volume) of air in the airways, lungs and in the ventilator system of the dummy and the hoses connecting the dummy to the ventilator and monitoring device for measurement of gas flow, oxygen concentration, etc. This volume in the test setup is around 800 ml, which exceeds that of a child (which is around 40 ml/kg).

It can be seen for all curves that by supplying 100% oxygen continuously via the hoses a fast increase in the oxygen concentration in the lungs can be expected reaching a constant level (at constant conditions) within minutes. It can be seen that the gas provided by the hoses (100% oxygen) is substantially mixed before reaching the lungs with a resulting lung oxygen concentration in these examples between 40% and 53%.

As an example the "lowest curve"—designated 2 L·12INSP—discloses the oxygen concentration in the artificial lung of the dummy at conditions where the hoses provide a flow of 100% oxygen at a flow rate of 2 liters per minute. The child is breathing with a rate of 25 beats per minute and a tidal volume of 120 ml. The inspiratory flow rate is 12 liters per minute. A resulting averaged oxygen concentration in the lungs of around 40% can be expected.

It is possible to make tests in clinical practice similar to tests performed with a dummy, as exemplified above, in order to get the results as disclosed in FIG. 7 which couples the flow rate and the oxygen percentage. Thus, when knowing tidal volume and the respiratory rate of the child; the flow rate can be selected, based on these results, for providing the desired oxygen percentage.

The result from the tests shows that the present invention can supply an enriched gas with a clinically relevant average oxygen percentage to a child. Further, it avoids the delivery of 100% oxygen (which is potentially toxic and should be avoided for other medical reasons (absorption atalectasis, a.o.)). These mixing capabilities is demonstrated with athmospheric air as ambient gas and 100% oxygen being provided by the hoses at flow rates up to 4 liters per minute.

REFERENCE LIST

1 body forming a mixing chamber
2 gas delivering hose
3 penetrating hole
4 gas inlet
5 gas outlet
6 opening
7 flexible band
8 edge portion
9 indentation
10 contact section of the edge portion
11 soother
12 teat
13 mouth shield
14 handle
15 supply hose

The invention claimed is:

1. A soother for delivering a gas mixture to the nasal airways of a spontaneously breathing child, the soother comprising:
   a teat;
   a mouth shield comprising a handle;
   a mixing chamber attached to the handle;
   at least two gas delivering hoses attached to the mixing chamber for supplying gas to the mixing chamber, wherein one or more of the at least two gas delivering hoses engage around at least a part of the handle of the soother; and
   the mixing chamber having access to air surrounding the soother and being adapted for mixing the supplied gas with the surrounding air in order to provide a gas mixture for nasal inhalation.

2. A soother according to claim 1, further comprising a flexible band attaching the mixing chamber to the soother.

3. A soother according to claim 1, wherein the mixing chamber is an integral part of the soother such that the mixing chamber cannot be separated from the soother.

4. A soother according to claim 1, wherein the mixing chamber comprises an edge portion with a contact section adapted for being in contact with the nasal dorsum of a child.

5. A soother according to claim 4, wherein the teat of the soother protrudes further than the contact section of the edge portion of the mixing chamber.

6. A soother according to claim 1, wherein the mixing chamber is releasably attached to soother by use of a flexible band.

7. A method for delivering a gas mixture to a child comprising the steps of:
    providing a soother;
    providing a mixing chamber for attachment to the soother and for positioning over the nostrils of a child such that the child inhales, at least partly, a gas passing through the mixing chamber;
    supplying gas to the mixing chamber; and
    providing access for the surrounding air to the mixing chamber;
    wherein the mixing chamber is used for mixing the supplied gas and the surrounding air into a mixed gas to be inhaled by the child, the mixing chamber comprising at least two gas delivering hoses attached to the mixing chamber for supplying the gas to the mixing chamber, one or more of the at least two gas delivering hoses engaging around at least a part of the handle of the soother, and a flexible band configured for securing the mixing chamber to a handle of the soother.

8. A method according to claim 7, wherein the mixing chamber comprises an edge portion such that when the mixing chamber is positioned such that the access for the surrounding air, at least partly, is provided between the edge portion and the child.

9. A method according to claim 7, wherein the access to the surroundings is at least partly provided by at least one hole penetrating the mixing chamber.

10. A mixing chamber adapted for fitting to a handle of a soother, the mixing chamber comprising:
    at least two gas delivering hoses attached to a mixing chamber for supplying gas to the mixing chamber;
    a flexible band configured for securing the mixing chamber to a handle of a soother, one or more of the at least two gas delivering hoses engaging around at least a part of the handle of the soother; and
    the mixing chamber having access to surrounding air and is adapted for mixing the supplied gas with the surrounding, air, wherein the mixing chamber is positioned over nostrils of a child in order to provide a gas mixture for nasal inhalation.

11. A mixing chamber according to claim 10, wherein the mixing chamber is releasably attached to the soother by using the flexible band.

12. A mixing chamber according to claim 10, further comprising an edge portion with at least one non-contact section adapted for having no contact with the child when the mixing chamber is in use, and the at least one tact section providing the mixing chamber access to the surrounding air.

13. A mixing chamber according to claim 10, wherein the gas is supplied continuously via the at least two gas delivering hoses.

14. A mixing chamber according to claim 10, wherein the mixing chamber further includes at least one penetrating hole defined therein for providing access to the surrounding air.

15. A mixing chamber according to claim 14, further comprising an edge portion, wherein the at least one penetrating hole is provided in the mixing chamber at least 5 mm or approximately 10 mm from the edge portion.

16. A mixing chamber according to claim 10, further comprising an edge portion with a contact section adapted for being in contact with the nasal dorsum of the child.

17. A mixing chamber according to claim 10, wherein the gas which is supplied via the at least two gas delivering hoses is oxygen.

18. A mixing chamber according to claim 10, further comprising an edge portion having a substantially triangular or heart shaped peripheral shape.

19. A mixing chamber according to claim 10, wherein the at least two gas delivering hoses are adapted to engage with the soother for attaching the mixing chamber to the soother.

20. A mixing chamber according to claim 10, wherein the mixing chamber is made of a soft, resilient material.

21. A mixing chamber according to claim 20, wherein the mixing chamber is made of silicone.

22. A mixing chamber according to claim 20, further comprising an edge portion, wherein the mixing chamber is softer along the edge portion than in a central portion.

23. A mixing chamber according to claim 22, wherein the edge portion is formed of a thinner material than the central portion, thereby providing the softer edge portion.

24. A mixing chamber according to claim 10, wherein the mixing chamber has a dome shape.

25. A mixing chamber according to claim 10, wherein the mixing chamber comprises a mesh.

26. A mixing chamber according to claim 10, wherein the at least two gas delivering hoses are adapted to be guided over the jaw region and away from the face of the child.

* * * * *